United States Patent [19]

Bank

[11] Patent Number: 5,283,348
[45] Date of Patent: Feb. 1, 1994

[54] PROCESS FOR PREPARATION OF BETA-CYANOALKYLSILANES

[75] Inventor: Howard M. Bank, Freeland, Mich.

[73] Assignee: Dow Corning Corporation, Midland, Mich.

[21] Appl. No.: 87,562

[22] Filed: Jul. 9, 1993

[51] Int. Cl.$^5$ ............................................. C07F 7/10
[52] U.S. Cl. ................................................. 556/415
[58] Field of Search ........................................ 556/415

[56] References Cited

U.S. PATENT DOCUMENTS

| | | | |
|---|---|---|---|
| 2,906,764 | 9/1959 | Jex et al. | 556/415 |
| 2,971,970 | 2/1961 | Bluestein | 556/415 |
| 2,971,972 | 2/1961 | Bluestein | 556/415 |
| 3,018,300 | 1/1962 | Pike | 556/415 |
| 3,030,403 | 4/1962 | Pike | 556/415 |
| 3,046,292 | 7/1962 | Pike | 556/415 |
| 5,103,033 | 4/1992 | Bank | 556/415 |
| 5,126,468 | 6/1992 | Bank | 556/415 |
| 5,126,469 | 6/1992 | Bank | 556/415 |

OTHER PUBLICATIONS

Svoboda et al., Collection Czechoslov, Chem. Commun. 38:3834–3836, 1973.
Rajkumar et al., Organometallics 8:549–550, 1989.

*Primary Examiner*—Paul F. Shaver
*Attorney, Agent, or Firm*—William F. Boley

[57] ABSTRACT

The present invention is a process for the preparation of hydrolyzable β-cyanoalkylsilanes. More particularly this invention is a process for the catalytic addition of silicon hydrides to α,β-unsaturated olefinic nitriles to form β-cyanoalkylsilanes. The present process employs a novel catalyst comprising an aminoorganosilane and a copper source. The catalyst may be provided to the process on a solid support.

26 Claims, No Drawings

PROCESS FOR PREPARATION OF BETA-CYANOALKYLSILANES

BACKGROUND OF INVENTION

The present invention is a process for the preparation of hydrolyzable beta-cyanoalkylsilanes. More particularly, this invention is a process for the catalytic addition of silicon hydrides to $\alpha,\beta$-unsaturated olefinic nitriles to form $\beta$-cyanoalkylsilanes. The present process employs a novel catalyst comprising an aminoorganosilane and a copper source. The catalyst may be provided to the process on a solid support.

Hydrolyzable $\beta$-cyanoalkylsilanes prepared by the present process are useful for the production of polyorganosiloxanes containing the $\beta$-cyanoalkyl substituent. The silicon-bonded $\beta$-cyanoalkyl radical is extremely resistant to hydrolysis and cleavage under hot, humid conditions. Therefore, the $\beta$-cyanoalkylsilanes find particular use in the preparation of polyorganosiloxanes which must be subjected to hot, humid conditions. The presence of the silicon-bonded $\beta$-cyanoalkyl radical substituted on polyorganosiloxanes also tends to stabilize the polyorganosiloxanes against swelling induced by liquid hydrocarbons.

Bluestein, U.S. Pat. No. 2,971,970, issued Feb. 14, 1961, describes a process for preparing cyanoalkylsilanes which comprises reacting a hydrolyzable silicon hydride with an $\alpha,\beta$-unsaturated olefinic nitrile in the presence of a diamine, a tertiary amine and a cuprous compound selected from the class consisting of cuprous oxide and cuprous halides.

Bluestein, U.S. Pat. No. 2,971,972, issued Feb. 14, 1961, describes a process for adding phenyldichlorosilane to acrylonitrile in the presence of a catalyst composition consisting essentially of a trialkylamine and a cuprous compound selected from the group consisting of cuprous halides and cuprous oxide.

Svoboda et al., Collection Czechoslov. Chem. Commun. 38:3834–3836, 1973, describe binary systems of a copper compound ($Cu_2O$, CuCl, or $Cu(acac)_2$) and an isocyanide (tert-butyl or cyclohexyl isocyanide) as effective catalysts for hydrosilation of acrylonitrile by trichlorosilane and methyldichlorosilane.

Rajkumar et al., Organometallics 8:550–552, 1989, describes a two-component catalyst, consisting of cuprous oxide and tetramethylethylenediamine, that promotes $\beta$-hydrosilylation of acrylonitrile.

SUMMARY OF INVENTION

The present invention is a process for the preparation of hydrolyzable $\beta$-cyanoalkylsilanes. More particularly this invention is a process for the catalytic addition of silicon hydrides to $\alpha,\beta$-unsaturated olefinic nitriles to form $\beta$-cyanoalkylsilanes. The present process employs a novel catalyst comprising an aminoorganosilane and a copper source. The catalyst may be provided to the process on a solid support.

DESCRIPTION OF INVENTION

The present invention is a process for preparation of $\beta$-cyanoalkylsilanes described by formula:

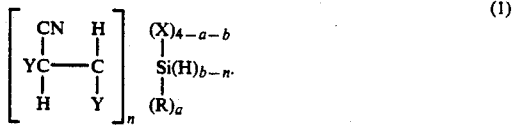

The process comprises contacting a silicon hydride described by formula $$R_aH_bSiX_{4-a-b}; \qquad (2)$$

with an $\alpha,\beta$-unsaturated olefinic nitrile described by formula $$YCH=CCN; \qquad (3)$$
$$\phantom{YCH=C}|\phantom{CN}$$
$$\phantom{YCH=C}Y$$

in the presence of a catalyst comprising an aminoorganosilane described by formula $$R_dSiR^1NR^2_2 \qquad (4)$$

and a copper source; at a temperature within a range of about 50° C. to 200° C.; where each R is independently selected from a group consisting of monovalent hydrocarbon radicals comprising one to 20 carbon atoms, substituted monovalent hydrocarbon radicals comprising one to 20 carbon atoms, alkoxy radicals comprising one to 20 carbon atoms, and aryloxy radicals; $R^1$ is selected from a group consisting of bivalent hydrocarbon radicals comprising one to 20 carbon atoms, and substituted bivalent hydrocarbon radicals comprising one to 20 carbon atoms; each $R^2$ is independently selected from a group consisting of hydrogen, monovalent hydrocarbon radicals comprising one to 20 carbon atoms, substituted monovalent hydrocarbon radicals comprising one to 20 carbon atoms, aminoalkyl radicals were each alkyl comprises one to 20 carbon atoms, alkylaminoalkyl radicals where each alkyl comprises one to 20 carbon atoms, alkylaminodialkyl radicals where each alkyl comprises one to 20 carbon atoms, dialkylaminoalkyl radicals where each alkyl comprises one to 20 carbon atoms, and polyaminoalkyl radicals where each alkyl comprises one to 20 carbon atoms; X is a halogen; each Y is independently selected from a group consisting of hydrogen and alkyl radicals comprising one to eight carbon atoms; n=1, 2, or 3; a=0, 1, or 2; b=1, 2, or 3; a+b=1, 2, or 3; and d=0, 1, 2, or 3.

The present process is applicable for the production of $\beta$-cyanoalkylsilanes containing one, two, or three silicon bonded $\beta$-cyanoalkyl radicals, as described by formula (1). Beta-cyanoalkylsilanes that can be made by the present process are, for example, bis($\beta$-cyanoethylmethyl)dichlorosilane, $\beta$-cyanoethylethyldichlorosilane, $\beta$-cyanopropyltrichlorosilane, $\beta$-cyanobutyloctyldichlorosilane, $\beta$-cyanoethylphenyldichlorosilane, $\beta$-cyanoethyldiphenylchlorosilane, $\beta$-cyanoethylmethylphenylchlorosilane, $\alpha$-ethyl-$\beta$-cyanoethylmethyldichlorosilane, $\beta$-cyanoethylvinyldichlorosilane, $\beta$-cyanoethylchlorosilane, $\beta$-cyanoethylmethyldibromosilane, $\beta$-cyanoethyltribromosilane, and $\beta$-cyanoethylmethyldifluorosilane, The silicon hydride of the present invention, described by formula (2), must contain one, two, or three silicon-bonded hydrogens. The silicon hydride must also contain one, two, or three halogen atoms. The halogen atom, X, can be selected from a group consisting of bromine, chlorine, fluorine, and iodine. The preferred halogen atom is chlorine.

The silicon hydride described by formula (2) can contain zero, one, or two radicals R. Each R radical is independently selected from a group consisting of monovalent hydrocarbon radicals comprising one to 20 carbon atoms, substituted monovalent hydrocarbon radicals comprising one to 20 carbon atoms, alkoxy radicals comprising one to 20 carbon atoms, and aryloxy radicals. The radical R can be alkyls, for example, methyl, ethyl, propyl, butyl, tert-butyl, pentyl, hexyl, heptyl, octyl, nonyl, decyl, pentadecyl, octadecyl, and eicosyl. The preferred alkyl is when R comprises one to eight carbon atoms. Most preferred is when R is methyl. The radical R can by aryls, for example, phenyl, naphthyl, diphenyl, tolyl, xylyl, cumenyl, ethylphenyl, and vinylphenyl. The preferred aryl is phenyl. The radical R can be aralkyls, for example, benzyl, and phenylethyl; haloaryls, for example, chlorophenyl, dibromophenyl, and chloronaphthyl; cyanoalkys, for example, β-cyanoethyl, β-cyanopropyl, and β-cyanobutyl; cycloalkyls, for example, cyclopentyl, cyclohexyl, and cycloheptyl; cyanocycloalkys, for example, cyanocyclobutyl and cyanocycloheptyl; alkenyls, for example, vinyl and allyl; substituted alkyls, for example, 3,3,3-trifluoropropyl; alkoxys, for example, methoxy, ethoxy, and propoxy; and aryloxy, for example, phenoxy. The preferred silicon hydride is selected from a group consisting of methyldichlorosilane and trichlorosilane.

The silicon hydride is contacted with an α,β-unsaturated olefinic nitrile described by formula (3). The α,β-unsaturated olefinic nitrile contains substituents Y, where each Y is independently selected from a group consisting of hydrogen and alkyls comprising one to eight carbon atoms. For example, Y can be methyl, ethyl, propyl, butyl, tert-butyl, pentyl, hexyl, heptyl, and octyl. Examples of the α,β-unsaturated olefinic nitriles useful in the present process include acrylonitrile, methacrylonitrile, crotononitrile, ethylacrylonitrile, 1-cyanobutene-1, and 2-cyanooctene-1.

The molar ratio of the silicon hydride to the unsaturated olefinic nitrile may be varied within wide limits. However, it is preferred that the molar ratio of hydrogen bonded to the silicon of the silicon hydride to α,β-unsaturated olefinic nitrile be within a range of about 0.1 to 2.0. Most preferred is when the molar ratio of hydrogen bonded to the silicon of the silicon hydride to α,β-unsaturated olefinic nitrile be within a range of about 0.9 to 1.1.

The silicon hydride and unsaturated olefinic nitrile are contacted in the presence of a catalyst comprising an aminoorganosilane and a copper source. The aminoorganosilanes useful in the present process are described by formula (4), where R is as previously described. The aminoorganosilane contains substituent R¹, where R¹ is selected from a group consisting of bivalent hydrocarbon radicals comprising one to 20 carbon atoms and substituted bivalent hydrocarbon radicals comprising one to 20 carbon atoms. The substituent R¹ can be, for example, methylene, ethylene, propylene, isobutylene, butylene, pentylene, hexylene, and benzylene. The aminoorganosilane contains substituents R², where each R² is independently selected from a group consisting of hydrogen, monovalent hydrocarbon radicals comprising one to 20 carbon atoms, substituted monovalent hydrocarbon radicals comprising one to 20 carbon atoms, aminoalkyl radicals where each alkyl comprises one to 20 carbon atoms, alkylaminoalkyl radicals where each alkyl comprises one to 20 carbon atoms, alkylaminodialkyl radicals where each alkyl comprises one to 20 carbon atoms, dialkylaminoalkyl radicals where each alkyl comprises one to 20 carbon atoms, and polyaminoalkyl radicals where each alkyl comprises one to 20 carbon atoms. The radical R² can be, for example, hydrogen, methyl, ethyl, propyl, tert-butyl, phenyl, and 3,3,3-trifluoropropyl. The Radical R² can be aminoalkyl radicals, for example, aminomethyl, and aminopropyl; and alkylaminoalkyl radicals, for example, N'-methylaminomethyl, N'-methylaminoethyl, N'-ethylaminomethyl, N'-ethylaminomethyl, and N,-methylaminohexamethyl. The radical R² can be an alkylaminodialkyl, for example, a radical with the formula

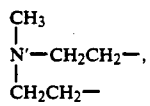

which can bond with the nitrogen atom of the aminoorganosilane to form a methylpiperzinyl radical. The radical R² can be a dialkylaminoalkyl, for example, N',N',-dimethylaminomethyl, N',N'-dimethylaminoethyl, N',N',-diethylaminomethy, N'-methyl-N'-ethylaminoethyl, N',N'-dimethylaminopropyl, and N'-methyl-N'-octylaminoethyl. The radical R² can be polyaminoalkyl radicals described by formula $\{(CH_2)_eN(A)\}_fA$, where A is selected from a group consisting of hydrogen and alkyls comprising one to eight carbon atoms, e is an integer from one to six, and f is an integer from one to 20. Examples of polyaminoalkyl radicals useful in the present process include N'',N''-dimethylaminoethyl-N'-methylaminoethyl; N'',N''-dimethylaminoethylaminoethyl; N''-methylaminoethyl-N''-methylaminopropyl-N'-methylaminoethyl; N'''-ethylaminoethyl-N'-ethylaminoethyl, and N''-methylaminopropyl-N'-methylaminopropyl. Preferred is when the radical R² is selected from a group consisting of methyl and N',N'-dimethylaminoethyl. Most preferred is when one radical R² is methyl and the second radical R² is N',N'-dimethylaminoethyl.

In the examples above, the primes denoting the location of pendant groups on the nitrogen atoms of the radicals R² and are numbered as they would be numbered in the aminoorganosilane according to the nomenclature used below to describe examples of the aminoorganosilane.

Examples of the aminoorganosilane include N-methylaminopropyltrimethoxysilane {i.e. (CH₃O)₃SiCH₂CH₂CH₂N(H)CH₃}, N,N-dimethylaminopropyltrimethoxysilane {i.e. (CH₃O)₃SiCH₂CH₂CH₂N(CH₃)₂}, N',N'-dimethylaminoethylaminopropyltrimethoxysilane {i.e. (CH₃O)₃SiCH₂CH₂CH₂N(H)CH₂CH₂N(CH₃)₂}, N,N-dimethylaminoethylmethyldimethoxysilane {i.e. (CH₃O)₂CH₃SiCH₂CH₂N(CH₃)₂}, N',N'-dimethylaminoethyl-N-methylaminopropyltrimethoxysilane {i.e. (CH₃O)₃SiCH₂CH₂CH₂N(CH₃)CH₂CH₂N(CH₃)₂}, N',N'dimethylaminopropyl-N-methylaminopropyltrimethoxysilane. N',N'-dimethylaminoethyl-N-methylaminopropyltrimethylsilane, N'''-methylaminoethyl-N'-methylaminoethyl-N-methylaminoethyltrimethoxysilane {i.e. (CH₃O)₃

SiCH$_2$CH$_2$N(CH$_3$)CH$_2$CH$_2$N(CH$_3$)CH$_2$CH$_2$N(H)CH$_3$.}, N''',N''-diethylaminoethyl-N'-ethylaminoethylaminopropylmethyldimethoxysilane {i.e. (CH$_3$O)$_2$CH$_3$SiCH$_2$CH$_2$CH$_2$N(H)CH$_2$CH$_2$N(CH$_2$CH$_3$)CH$_2$CH$_2$N(CH$_2$CH$_3$)$_2$}, N-methylaminopropyltrimethoxysilane {i.e. (CH$_3$O)$_3$SiCH$_2$CH$_2$CH$_2$N(H)CH$_3$}, and N'-methyl-N-piperzinylpropylmethyldimethoxysilane {i.e.
CH$_3$(CH$_3$O)$_2$SiCH$_2$CH$_2$CH$_2$NCH$_2$CH$_2$N(CH$_3$)CH$_2$CH$_2$ ⌐
                                                                    └────────────┘

The most preferred aminoorganosilane is N',N'-dimethylaminoethyl-N-methylaminopropyltrimethoxysilane.

The aminoorganosilane can be retained on a solid support. The method of retention of the aminoorganosilane on the solid support is not critical to the present invention. It is preferred that the aminoorganosilane not be released from the solid support during conduct of the process. The aminoorganosilane may be retained on the solid support by standard means, for example, adsorption, ionic bonding, covalent bonding, or physical entrapment. The preferred method of retaining the aminoorganosilane on the solid support is by covalent bonding.

The solid support can be any material capable of retaining the aminoorganosilane under process conditions. The solid support can be, for example, silica gel, aluminum oxide, mixtures of aluminum oxide and chromium oxide, mixtures of aluminum oxide and tungsten oxide, sodium zeolite magnesium oxide, zinc oxide, titanium oxide, magnesium silicate, aluminum silicate, calcium silicate, and glass. The preferred solid support is silica gel.

The solid support can be in the form of, for example, flakes, chips, particles, powders, pellets, and tablets. It is preferred that the solid support by less than about one centimeter in diameter. It is more preferred that the solid support be less than about 0.5 centimeter in diameter. Generally, the lower size limit for the diameter of the solid support is determined by the ability to obtain and handle the material.

A useful concentration of aminoorganosilane retained on the solid support is where the weight of aminoorganosilane is within a range of about one to 50 weight percent of the combined weight of the solid support and aminoorganosilane. Preferred is when the concentration of aminoorganosilane retained on the solid support is within a range of about five to 30 weight percent of the combined weight of the solid support and aminoorganosilane.

The quantity of the aminoorganosilane employed in the present process in relation to the α,β-unsaturated olefinic nitrile may be varied within wide limits. In general, the process can be run under conditions where the mole ratio of the aminoorganosilane to α,β-unsaturated olefinic nitrile is within a range of about 0.001 to 1.0. A preferred mole ratio of the aminoorganosilane to unsaturated olefinic nitrile is within a range of about 0.01 to 0.1.

The catalyst employed in the present process also comprises a copper source. The copper source can be copper metal, copper compound, or a mixture of the two. The copper metal can be added to the process as a particulate, for example, a powder. Although the particle size of the copper metal is not critical, it preferred that the copper metal be added to the process as a powder having an average particle diameter less than about 0.15 mm. More preferred is when the copper metal is added to the process as a powder having an average particle diameter less the about 0.05 mm.

Copper compounds added to the process can be either inorganic or organic compounds of copper(I) and copper(II). The inorganic copper compound can be selected from a group consisting of, for example, copper halide, copper oxide, copper sulfate, copper sulfide, copper cyanide, Cu(I) thiocyanide, and copper chromium compounds. The copper halide compound can be, for example. Cu(I) chloride. Cu(I) bromide, Cu(I) iodide, Cu(I) fluoride, Cu(II) chloride, Cu(II) bromide, Cu(II) iodide, and Cu(II) fluoride. The copper oxide compound can be, for example, Cu(I) oxide and Cu(II) oxide. The copper sulfate compound can be, for example, Cu(I) sulfate and Cu(II) sulfate. The copper sulfide compound can be, for example, Cu(I) sulfide and Cu(II) sulfide. The copper cyanide compound can be, for example, Cu(I) cyanide and Cu(II) cyanide. The copper chromium compounds can be, for example, Cu(II) chromate such as CuCrO$_4$.2CuO.2H$_2$O; Cu(II) dichromate such as CuCr$_2$O$_7$.2H$_2$O; and Cu(I) chromite such as Cu$_2$Cr$_2$O$_4$(2CuOCr$_2$O$_3$).

The preferred inorganic copper compound is selected from a group consisting of Cu(I) chloride. Cu(II) chloride, Cu(I) oxide, and Cu(II) oxide. The most preferred inorganic copper compound is Cu(I) chloride.

The copper compound can be an organic copper compound. When the copper compound is an organic compound, it is preferred that each organic substituent of the organic copper compound comprise less than about 25 carbon atoms. Preferred is when the organic copper compound is a di-coordinate organic copper compound. The term "di-coordinate organic copper compound" means a compound of general formula Cu(R$^3$)$_2$; where R$^3$ is selected from the group consisting of aryl radicals and radicals of formula —OR$^4$, —OOCR$^4$, and —O—(R$^5$)C=C—(R$^5$)C=O; where R$^4$ is selected from a group consisting of alkyl, alkenyl, and aryl radicals of less than 25 carbon atoms and R$^5$ is selected from a group consisting of hydrogen and hydrocarbon radicals of less than seven carbon atoms.

The di-coordinate organic copper compound can be, for example, Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) naphthanate, and Cu(II) phenylate.

The copper compounds may be soluble or insoluble in the process depending on the compounds which are present in the reaction mixture.

The aminoorganosilane and copper source can be precontacted and added to the process together, or the aminoorganosilane and copper source can be added separately to the process.

The amount of copper source added to the process can be that which provides about 0.01 to 100 moles of copper per mole of aminoorganosilane. It is preferred that the amount of copper in the process be within a range of about 0.1 to 5 moles per mole of aminoorganosilane.

In a preferred method for conducting the presence process, the process is conducted in an essentially oxygen free environment. The reduction of free oxygen in the process can increase the reaction rate and improve process yield. The term "essentially oxygen-free environment" means the free oxygen content of the environment in which the process is run is reduced below that of normal air. By "free oxygen," it is meant oxygen that is not present in combination with other elements. It is preferred that the essentially oxygen-free environment contain less than about 0.5 volume percent free oxygen.

The reactor can be reduced in free oxygen by standard means, for example, purging with an inert gas such as nitrogen, argon, or helium or by vacuum evacuation. Preferred is when the reactor is purged with argon.

The present process can be conducted in any suitable reactor of standard design. It is preferred that the reactor be formed from materials that are not reactive in the process and that the reactor be capable of maintaining an essentially oxygen free environment. The process can be run as a batch process or as a continuous process. A preferred process is where the reaction is conducted under homogeneous conditions in a continuous-flow pressure coil. Although not necessary, it is preferred that the contents of the reactor be mixed when the process is run as a batch process. Mixing can be accomplished by standard means, for example, mechanical stirring, refluxing, sonification, or turbulent flow.

The temperature at which the present process can be conducted is within a range of about 50° C. to 200° C. It is preferred that the temperature be within a range of about 100° C. to 180° C. Generally, higher temperatures allow the use of a lower catalyst concentration, but at temperatures above about 180° C. lower yield may result.

The time required for conducting the process will vary depending on, for example, the particular silicon hydride, $\alpha,\beta$-unsaturated olefinic nitrile, catalyst and catalyst concentration employed, as well as the process temperature. In general, reaction times within a range of about 0.1 hour to 100 hours are considered useful. A preferred reaction time is within a range of about 0.5 hour to 15 hours.

The following examples are provided to illustrate the present invention. These examples are not intended to limit the claims herein.

EXAMPLE 1

The ability of a catalyst comprising cuprous(I) chloride and N,N-dimethylaminopropyltrimethoxysilane to catalyze the reaction of methyldichlorosilane with acrylonitrile was evaluated. The process was conducted in a 8 mm I.D. by 35 cm sealed glass tube. A mixture consisting of 2.0 ml of a 1.1 molar ratio of methyldichlorosilane to acrylonitrile was placed in the tube. N,N-dimethylaminopropyltrimethoxysilane was added to the tube to provide a 0.033 molar ratio with the acrylonitrile and a 1.9 molar ratio with cuprous(I) chloride added to the tube. The tube was purged with argon, sealed, and heated at 120° C. for about 19 hours. At the end of the heating period, the content of the tube was cooled and analyzed by gas liquid chromatography (GLC) using a flame ionization detector (FID). Beta-cyanoethylmethyldichlorosilane was determined to be 0.013 percent of the total area under the GLC-FID trace.

EXAMPLE 2

The ability of a catalyst comprising cuprous(I) chloride and N',N'-dimethylaminoethyl-N-methylaminopropyltrimethoxysilane to catalyze the reaction of methyldichlorosilane with acrylonitrile was evaluated. The process was conducted in a sealed glass tube as described in Example 1. A mixture consisting of 2.0 ml of a 1.1 molar ratio of methyldichlorosilane to acrylonitrile was placed in the tube. N',N'-dimethylaminoethyl-N-methylaminopropyltrimethoxysilane was added to the tube to provide a 0.033 molar ratio with the acrylonitrile and a 1.8 molar ratio with cuprous(I) chloride added to the tube. The tube was purged with argon, sealed, and heated at 120° C. for about 23 hours. After heating the content of the tube was analyzed by GLC-FID as described in Example 1. Beta-cyanoethylmethyldichlorosilane represented 60.5 area percent of the total area under the GLC-FID trace.

EXAMPLE 3

The ability of a catalyst comprising cuprous(I) chloride and N',N'-dimethylaminoethyl-N-methylaminopropyltrimethoxysilane supported on silica gel to catalyze the reaction of trichlorosilane with acrylonitrile was evaluated. The supported catalyst was formed by mixing about 30 g of silica gel (Davison Chemical. Baltimore, Md.) with approximately 300 ml of toluene and refluxing this mixture at 108° C. for two hours in an argon purged vessel. After two hours of refluxing, 9.0 g of N',N'-dimethylaminoethyl-N-methylaminopropyltrimethoxysilane was added to reaction vessel. The contents of the reaction vessel was then heated for an additional seven hours with stirring. The silica gel supported aminoorganosilane was then extracted with toluene for about five hours, washed with toluene, and dried at room temperature for six hours under vacuum. The resulting product consisted of about 20 weight percent aminoorganosilane as a percent of the combined weight of the silica gel and the aminoorganosilane.

The catalytic activity of a mixture comprising cuprous(I) chloride and the supported aminoorganosilane was then evaluated in sealed glass tubes as described in Example 1. A mixture consisting of 2.0 ml of a 1.27 molar ratio of trichlorosilane to acrylonitrile was placed in the tube. The supported N',N'-dimethylaminoethyl-N-dimethylaminoethyl-N-methylaminopropyltrimethoxysilane was added to the tube to provide a 0.043 molar ratio with the acrylonitrile and a 2.2 molar ratio with cuprous(I) chloride added to the tube. The tube was purged with argon, sealed, and heated at about 104° C. for 1.5 hours. After heating the content of the tube was analyzed by GLC using a thermal conductivity detector (TCD). Beta-cyanoethyltrichlorosilane represented 56.4 area percent of the total area under the GLC-TCD trace.

EXAMPLE 4

The ability of a catalyst comprising cuprous(I) chloride and N,N-dimethylaminopropyltrimethoxysilane supported on silica gel to catalyze the reaction of methydichlorosilane with acrylonitrile was evaluated. The supported aminoorganosilane was prepared by a method similar to that described in Example 3. N,N-dimethylaminopropyltrimethoxysilane comprised about 12 weight percent of the combined weight of the silica gel and aminoorganosilane. A mixture consisting of 2.0 ml of a 1.1 molar ratio of methydichlorosilane to acrylonitrile was placed in tube as described in Example 1. The supported aminoorganosilane was added to the tube to provide a 0.033 molar ratio with the acrylonitrile and a 1.82 molar ratio with cuprous(I) chloride added to the tube. The tube was purged with argon, sealed, and heated at about 120° C. for about 20 hours. After heating the content of the tube was analyzed by GLC-FID as described in Example 1. Beta-cyanoethylmethyldichlorosilane represented 3.1 area percent of the total area under the GLC-FID trace.

EXAMPLE 5

The ability of a catalyst comprising cuprous(I) chloride and N'-methyl-N-piperzinylpropylmethyl-dimethoxysilane supported on silica gel to catalyze the reaction of methyldichlorosilane with acrylonitrile was evaluated. The supported aminoorganosilane was prepared by a method similar to that described in Example 3. N'-methyl-N-piperazinylpropylmethldimethoxsilane comprised about 12 weight percent of the combined weight of the silica gel and aminoorganosilane. A mixture consisting of 2.0 ml of a 1.1 molar ratio of methyldichlorosilane to acrylonitrile was placed in tube as described in Example 1. The supported aminoorganosilane was added to the tube to provide a 0.033 molar ratio with the acrylonitrile and a 1.80 molar ratio with cuprous(I) chloride added to the tube. The tube was purged with argon, sealed, and heated at about 120° C. for about 20 hours. After heating the content of the tube was analyzed by GLC-FID as described in Example 1. Beta-cyanoethylmethyldichlorosilane represented 0.7 percent of the total area under the GLC-FID trace.

EXAMPLE 6

The ability of a catalyst comprising cuprous(I) chloride and N',N'-dimethylaminoethyl-N-methylaminopropyltrimethoxysilane supported on silica gel to catalyze the reaction of methydichlorosilane with acrylonitrile was evaluated. The supported aminoorganosilane was prepared by a method similar to that described in Example 3. N',N'-dimethylaminoethyl-N-methylaminopropyltrimethoxysilane comprised about 20 weight percent of the combined weight of the silica gel and aminoorganosilane. A mixture consisting of 2.0 ml of a 1.1 molar ratio of methyldichlorosilane to acrylonitrile was placed in a tube as described in Example 1. The supported aminoorganosilane was added to the tube to provide a 0.029 molar ratio with the acrylonitrile and a 1.77 molar ratio with cuprous(I) chloride added to the tube. The tube was purged with argon, sealed, and heated at 170° C. for about 20 hours. After heating, the content of the tube was analyzed by GLC-FID as described In Example 1. Beta-cyanoethylmethyldichlorosilane represented 14.5 area percent of the total area under the GLC-FID trace.

I claim:

1. A process for preparation of beta-cyanoalkylsilanes described by formula

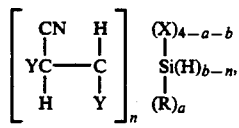

the process comprising: contacting a silicon hydride described by formula $$R_a H_b Si X_{4-a-b}$$

with an α,β-unsaturated olefinic nitrile described by formula

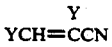

in the presence of a catalyst comprising an aminoorganosilane described by formula $$R_d Si R^1 N R^2{}_2$$

and a copper source; at a temperature within a range of about 50° C. to 200° C.; where each R is independently selected from a group consisting of monovalent hydrocarbon radicals comprising one to 20 carbon atoms, substituted monovalent hydrocarbon radicals comprising one to 20 carbon atoms, alkoxy radicals comprising one to 20 carbon atoms, and aryloxy radicals; $R^1$ is selected from a group consisting of bivalent hydrocarbon radicals comprising one to 20 carbon atoms, and substituted bivalent hydrocarbon radicals comprising one to 20 carbon atoms; each $R^2$ is independently selected from a group consisting of hydrogen, monovalent hydrocarbon radicals comprising one to 20 carbon atoms, substituted monovalent hydrocarbon radicals comprising one to 20 carbon atoms, aminoalkyl radicals were each alkyl comprises one to 20 carbon atoms, alkylaminoalkyl radicals where each alkyl comprises one to 20 carbon atoms, alkylaminodialkyl radicals where each alkyl comprises one to 20 carbon atoms, dialkylaminoalkyl radicals where each alkyl comprises one to 20 carbon atoms, and polyaminoalkyl radicals where each alkyl comprises one to 20 carbon atoms; X is a halogen; each Y is independently selected from a group consisting of hydrogen and alkyl radicals comprising one to eight carbon atoms; n=1, 2, or 3; a=0, 1, or 2; b=1, 2, or 3; a+b=1, 2, or 3; and d=0, 1, 2, or 3.

2. A process according to claim 1, where the halogen is chlorine.

3. A process according to claim 1, where R is methyl.

4. A process according to claim 1, where the silicon hydride is selected from a group consisting of methyldichlorosilane and trichlorosilane.

5. A process according to claim 1, where the α,β-unsaturated olefinic nitrile is selected from a group consisting of acrylonitrile, methacrylonitrile, crotononitrile, ethylacrylonitrile, 1-cyanobutene-1, and 2-cyanooctene-1.

6. A process according to claim 1, where the α,β-unsaturated olefinic nitrile is acrylonitrile.

7. A process according to claim 1, where the molar ratio of hydrogen bonded to silicon of the silicon hydride to α,β-unsaturated olefinic nitrile is within a range of about 0.1 to 2.0.

8. A process according to claim 1, where the molar ratio of hydrogen bonded to silicon of the silicon hydride to α,β-unsaturated olefinic nitrile is within a range of about 0.9 to 1.1.

9. A process according to claim 1, where the radical $R^2$ is selected from a group consisting of methyl and N',N'-dimethylaminoethyl.

10. A process according to claim 1, where a first $R^2$ radical is methyl and a second $R^2$ radical is N',N'-dimethylaminoethyl.

11. A process according to claim 1, where the aminoorganosilane is N',N'-dimethylaminoethyl-N-methylaminopropyltrimethoxysilane.

12. A process according to claim 1, where the aminoorganosilane is retained on a solid support.

13. A process according to claim 12, where the aminoorganosilane is retained on the solid support by covalent bonding.

14. A process according to claim 12, where the solid support is silica gel.

15. A process according to claim 12, where the weight of aminoorganosilane retained on the solid support is within a range of about five to 30 weight percent of the combined weight of the solid support and aminoorganosilane.

16. A process according to claim 1, where the mole ratio of the aminoorganosilane to $\alpha,\beta$-unsaturated olefinic nitrile is within a range of about 0.001 to 1.0.

17. A process according to claim 1, where the mole ratio of the aminoorganosilane to $\alpha,\beta$-unsaturated olefinic nitrile is within a range of about 0.01 to 0.1.

18. A process according to claim 1, where the copper source is an inorganic copper compound selected from a group consisting of Cu(I) chloride, Cu(II) chloride, Cu(I) oxide, and Cu(II) oxide, 19. A process according to claim 1, where the copper source is Cu(I) chloride.

20. A process according to claim 1, where the copper source is a di-coordinate organic copper compound selected from a group consisting of Cu(II) methoxide, Cu(II) ethoxide. Cu(II) allyloxide, Cu(II) acetate, Cu(II) stearate, Cu(II) tetramethylheptanedionate, Cu(II) acetylacetonate, Cu(II) naphthanate, and Cu(II) phenylate.

21. A process according to claim 1, where the copper source provides about 0.01 to 100 moles of copper per mole of aminoorganosilane.

22. A process according to claim 1, where the copper source provides about 0.1 to 5 moles of copper per mole of aminoorganosilane.

23. A process according to claim 1, where the process is conducted in an essentially oxygen free environment.

24. A process according to claim 1, where the process is conducted under homogeneous conditions in a continuous-flow pressure coil.

25. A process according to claim 1, where the process is conducted at a temperature within a range of about 100° C. to about 180° C.

26. A process according to claim 1, where reaction time for the process is within a range of about 0.5 hours to 15 hours.

* * * * *